United States Patent [19]

Ninomiya et al.

[11] Patent Number: 5,138,105
[45] Date of Patent: Aug. 11, 1992

[54] PROCESS AND APPARATUS FOR RECOVERING A LOWER ALCOHOL FROM A MIXTURE THEREOF WITH WATER

[75] Inventors: Masao Ninomiya; Masao Kikuchi, both of Ichihara; Masaru Umeda; Motojuro Yamaya, both of Tokyo, all of Japan

[73] Assignees: Ube Industries, Ltd.; M. Watanabe & Co., Ltd., both of Japan

[21] Appl. No.: 779,465

[22] Filed: Oct. 18, 1991

[30] Foreign Application Priority Data

Oct. 19, 1990 [JP] Japan .................................. 2-281329

[51] Int. Cl.$^5$ ..................... C07C 29/76; C07C 31/10; F26B 3/00; F26B 19/00
[52] U.S. Cl. ........................ 568/916; 34/22; 34/36; 34/243 R
[58] Field of Search ................. 568/916; 34/22, 36

[56] References Cited
U.S. PATENT DOCUMENTS 4,895,989 1/1990 Sander et al. .................. 568/916

Primary Examiner—J. E. Evans
Attorney, Agent, or Firm—Finnegan, Henderson, Farabow, Garrett & Dunner

[57] ABSTRACT

A lower alcohol is recovered from a mixed liquid thereof with water, derived from a vapor drying procedure for a water-wetted article, for example, a water-washed lens or semiconductor wafer, by feeding the mixed liquid of a lower alcohol with water from the vapor drying procedure to a vaporizer; vaporizing the mixed liquid; feeding the mixed vapor into a gas-separating module comprising at least one gas-separating membrane, for example, composed of a aromatic polyimide hollow fiber, which allows a selective permeation of water vapor from a feed side to a permeated side therethrough, withdrawing a non-permeated vapor fraction containing the lower alcohol in an increased concentration from the feed side, and converting the vapor fraction to a high purity lower alcohol liquid by cooling, while discharging a permeated vapor fraction containing water in an increased concentration from the permeated side.

15 Claims, 1 Drawing Sheet

PROCESS AND APPARATUS FOR RECOVERING A LOWER ALCOHOL FROM A MIXTURE THEREOF WITH WATER

BACKGROUND OF THE INVENTION

1. Field of the Invention

The present invention relates to a process and apparatus for recovering a lower alcohol from a mixture thereof with water. Particularly, the present invention relates to a process and apparatus for recovering a lower alcohol from a mixture thereof with water, derived from a vapor drying process for water-washed articles, for example, precision electronic components such as printed circuit boards, semiconductor wafers and electronic parts; and lenses. More particularly, the present invention relates to a process and apparatus for separating and recovering a lower alcohol from a mixed liquid thereof with water derived from a process in which a vapor of a lower alcohol is brought into contact with at least one article, for example, a precision electronic component, for a vapor drying of the article and the resultant mixed liquid of the lower alcohol with water is subjected to a vaporizing step and then to a gas-separating step in which the water vapor is separated by a gas-separating membrane to recover the lower alcohol at a high concentration.

2. Description of the Related Arts

It is known that certain water-wetted articles can be safely dried only by bringing the article into contact with a high temperature vapor of a volatile solvent, for example, isopropyl alcohol, generated by heating the solvent. This vapor drying process is disclosed, for example, by Japanese Unexamined Patent Publication No. 56-168072. Also, an apparatus for the vapor drying process is disclosed, for example, in Japanese Unexamined Patent Publication No. 58-207638.

The conventional vapor drying apparatus is provided with a region for generating a vapor of a treating liquid, for example, a lower alcohol, a region for treating at least one water-wetted article to be vapor dried, and a region for collecting the used treating liquid contaminated with water derived from the water-wetted article. To regenerate the treating liquid containing water collected in the collecting region, a refining apparatus provided with a means for removing water from the used treating liquid containing water, and with a vaporizing means, is connected to the collecting region for the used treating liquid.

Japanese Unexamined Patent Publication No. 62-106,630 discloses a vapor drying apparatus capable of introducing the resultant refined treating liquid to the vapor-generating region. This Japanese publication also discloses that the water-containing treating liquid derived from the vapor drying region in which a water-wetted article, for example, a semiconductor wafer, is dried with a vapor of a lower alcohol, is refined by a refining apparatus having a water-removing means and a distilling means, and the refined treating liquid is returned to the vapor-generating region to be reused as the treating liquid.

In the conventional vapor drying apparatus, however, the means for removing water from the water-containing treating liquid is not specifically disclosed but is considered to utilize a desiccant as a means for removing water from the water-containing treating liquid. In this case, there is a limitation to the treating capacity of the desiccant, and a reclaiming of the used desiccant becomes necessary.

Further, the above-mentioned conventional vapor-drying apparatus is disadvantageous in that the content of water in the used treating liquid, for example, lower alcohol, collected in a bottom portion of a vapor treating vessel is gradually increased, and finally, it become impossible to generate a vapor comprising the lower alcohol in a satisfactorily high concentration, and thus it is no longer effective for the vapor drying of the water-wetted articles from the collected treating liquid, due to a high concentration of water in the collected treating liquid. Therefore, fresh high purity lower alcohol must be successively supplied to the vapor drying apparatus and the used treating liquid containing water in an increased concentration must be continuously discharged from the vapor drying apparatus. Therefore, a practical economic and effective process for reclaiming the discharged water-containing treating liquid is not known.

SUMMARY OF THE INVENTION

An object of the present invention is to provide a process and apparatus for recovering a lower alcohol from a mixture thereof with water, derived from a vapor drying procedure for at least one water-containing article, in which procedure a vapor of the lower alcohol is used to dry the article and condensed together with water, the process and apparatus being able to easily recover the lower alcohol in a high purity, and optionally, return the recovered high purity lower alcohol to the vapor drying procedure to be reused therein.

The above-mentioned object can be attained by the process and apparatus of the present invention, wherein the process of the present invention for recovering a lower alcohol from a mixture thereof with water comprises the steps of:

(A) vapor-treating at least one article wetted at the surface thereof with water, and placed in a vapor treating vessel with a vapor of a lower alcohol generated from a corresponding lower alcohol-based liquid to vapor dry the article, while allowing the vapor of the lower alcohol to be condensed on the surface of the article;

(B) feeding a mixed liquid of the lower alcohol with water comprising the condensed liquid into a vaporizer to provide a mixed vapor of the lower alcohol with water;

(C) feeding the mixed vapor of the lower alcohol with water into a gas-separating module comprising therein at least one gas-separating membrane allowing a selective permeation of water vapor therethrough from a feed side to a permeated side thereof, to separate the mixed vapor into a non-permeated vapor fraction comprising the lower alcohol in an increased concentration and water in a reduce concentration and a permeated vapor fraction containing water in an increased concentration;

(D) recovering the non-permeated vapor fraction from the feed side of the gas-separating membrane, while discharging the permeated vapor fraction from the permeated side of the gas-separating membrane; and (E) cooling the recovered non-permeated vapor fraction to convert it to a liquid containing the lower alcohol in an increased concentration.

The apparatus of the present invention for recovering a lower alcohol from a mixture thereof with water comprises:

(a) a vapor treating vessel provided with a tank space located in the bottom thereof, in which space a lower alcohol-based liquid is contained, a heater for heating the lower alcohol-based liquid in the tank space, a holder located above the tank space, by which at least one article wetted at the suface thereof with water and to be vapor dried is held;

(b) a vaporizer provided with a bottom space connected to tank space of the vapor treating vessel, in which bottom space a mixed liquid of the lower alcohol with water supplied from the vapor treating vessel is contained, and a heater for heating the mixed liquid to generate a mixed vapor of the lower alcohol with water;

(c) a gas-separating module containing therein at least one gas-separating membrane through which water vapor selectively permeates from a feed side connected to the vaporizer to a permeated side of the membrane, to separate the mixed vapor into a permeated fraction containing water in an increased concentration and a non-permeated fraction containing the lower alcohol in an increased concentration;

(d) a cooling device connected to the feed side of the gas-separating membrane, by which cooling device the non-permeated fraction is converted to a liquid containing the lower alcohol in an increased concentration; and (e) means for discharging the permeated fraction containing water in an increased concentration from the permeated side of the gas separating membrane.

DESCRIPTION OF THE PREFERRED EMBODIMENTS

Figure 1:
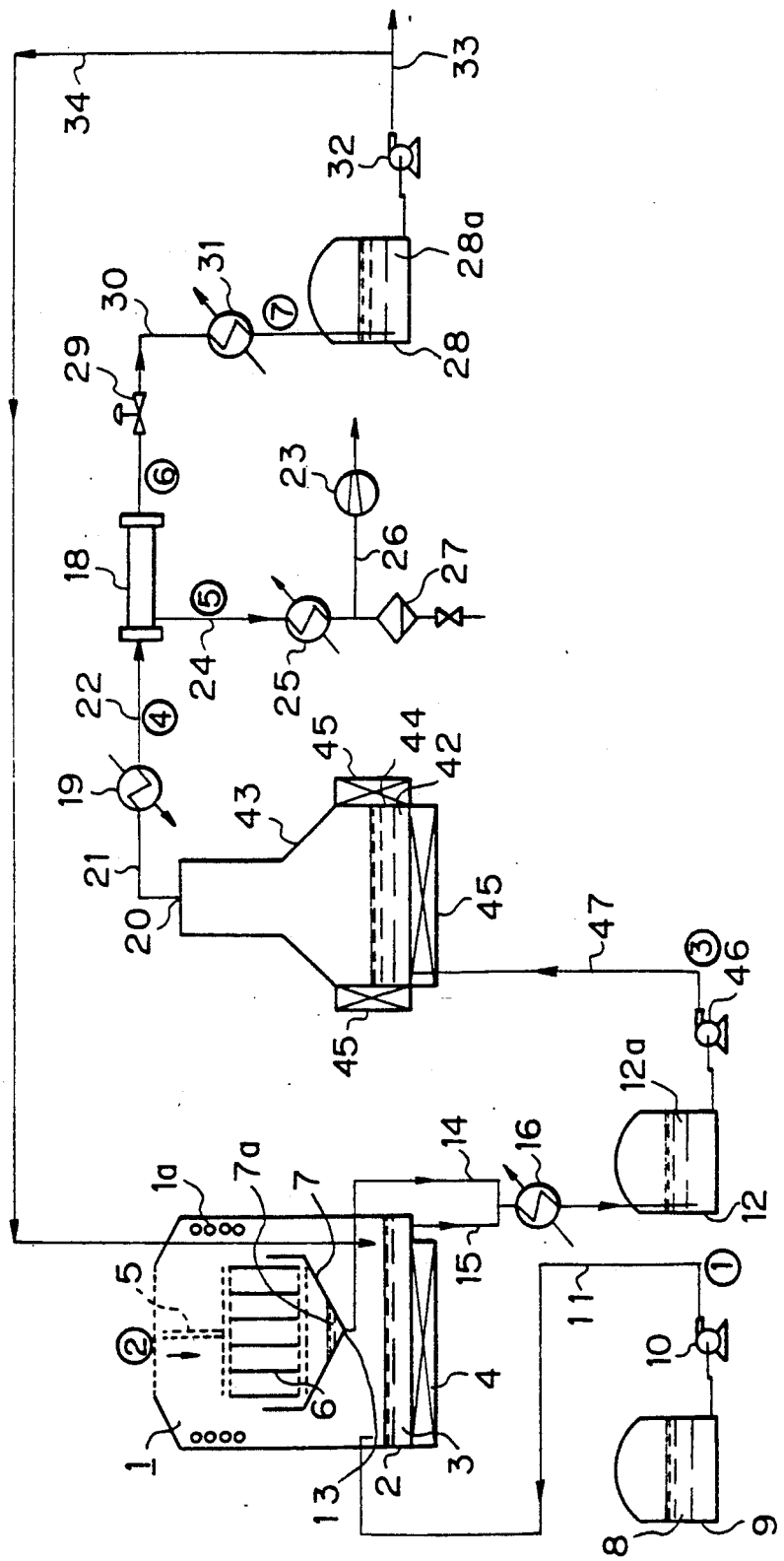
FIG. 1 is an explanatory flow sheet of an embodiment of the process of the present invention for recovering a lower alcohol from a mixture thereof with water, derived from a vapor drying procedure of at least one water-wetted article with a lower alcohol vapor.

The process and apparatus of the present invention are illustrated in FIG. 1.

Referring to FIG. 1, a vapor treating vessel 1 is provided with a tank space 2 located in the bottom thereof, for containing therein a lower alcohol-based liquid 3 containing a lower alcohol in a high concentration, a heater 4 attached to the tank space 2, for heating and vaporizing the lower alcohol-based liquid 3 in the tank space, and a holder 5 located above the tank space 2, by which at least one water-containing article 6 is held in the vapor treating vessel 1, and optionally a funnel-shaped collector 7 located between the holder 5 and the tank space 2, in which collector 7, a condensed mixed liquid of the lower alcohol with water is collected.

In the process of the present invention, a vapor treating step is carried out by using the vapor treating vessel. In the vapor treating step, a lower alcohol-based liquid 3 in the tank space 2 is heated by the heater 4 to generate a vapor of the lower alcohol. The water-containing article 6 held by the holder 5 is vapor dried by the lower alcohol vapor, and a resultant vapor of the lower alcohol is condensed on the surface of the article and optionally the resultant condensed liquid 7a is collected by the funnel shaped collector 7. The condensed liquid 7a contains water in an increased concentration.

If necessary, the vapor treating vessel 1 is provided with a cooling device 1a composed of, for example, a coiled cooling pipe, and arranged on the inside wall face of the vapor treating vessel 1. The cooling device 1a effectively promotes the condensation of the resultant mixture of the lower alcohol vapor with water vapor.

A fresh lower alcohol liquid 8 is fed from a tank 9 to the tank space 2 of the vapor treating liquid 1 through a pump 10 and a conduit 11.

This supply of the fresh lower alcohol liquid 8 is carried out to maintain the concentration of the lower alcohol in the lower alcohol-based liquid 3 in the tank space 2 at a high level of preferably 90% by weight or more, more preferably 95% by weight or more.

The fresh lower alcohol liquid preferably contains the lower alcohol in a high concentration of 98% by weight or more, more preferably 99% by weight or more, and water in a limited concentration of 2% by weight or less, more preferably, 1% by weight or less.

A mixed liquid tank 12 is arranged downstream of the vapor treating vessel 1 and connected to a bottom outlet 13 of the collector 7 in the vapor treating vessel 1 through a conduit 14, and optionally, to the tank space 2 through a conduit 15.

Optionally, a cooler 16 is arranged upstream of the mixed liquid tank 12.

The condensed liquid 7a is discharged from the collector 7 to the mixed liquid tank 12 through the conduit 14, and optionally, the cooler 16. If necessary, a portion of the lower alcohol-based liquid 3 is discharged from the tank space 2 through the conduit 15 and mixed with the condensed liquid 7a discharged from the collector 7, and the resultant mixture is received in the tank 12.

The partial discharge of the lower alcohol-based liquid 3 in the vapor treating vessel 1 is effective, together with the supply of the fresh lower alcohol liquid into the tank space 2, for maintaining the concentration of the lower alcohol in the lower alcohol-based liquid 3 at the above-mentioned high level.

The mixed liquid 12a received in the tank 12 preferably has a concentration of the lower alcohol of 75% by weight, more preferably 80% by weight or more. This concentration is effective for obtaining a lower alcohol having a high purity by a gas-separating procedure.

A vaporizer 43 has a bottom space 44 for containing therein a mixed liquid 42 supplied from the tank 12 and is provided with a heating device 45 attached to the bottom space 44. The mixed liquid tank 12 is connected to the bottom space 44 of the vaporizer 43 through a pump 46 and a conduit 47, and the liquid 12a is introduced into the bottom space 44 to form a mixed liquid layer 42 in the vaporizer 43. The mixed liquid 42 is heated and vaporized by the heating device 45 to generate a mixed vapor of the lower alcohol and water.

A gas-separating module 18 is arranged downstream of the vaporizer 43, and an overheater 19 is optionally arranged between the vaporizer 43 and the gas-separating module 18.

The mixed vapor of the lower alcohol with water generated in the vaporizer 43 is discharged from an outlet 20 of the vaporizer 43 through a conduit 21, and optionally, overheated by the overheater 19 to a predetermined temperature and then introduced into the gas-separating module 18 through a conduit 22.

The gas-separating module 18 is provided with at least one gas-separating membrane (not shown in the drawing) arranged therein. When the mixed vapor is introduced into the feed side of the gas-separating membrane, water vapor is allowed to selectively permeate from the feed side to a permeated side of the membrane, through the membrane, and the mixed vapor is separated into a permeated fraction and a non-permeated fraction. The permeated fraction contains water in an increased concentration and the non-permeated fraction contains the lower alcohol in an increased concentration and water in a reduced concentration.

The permeated side of the gas-separating membrane is connected to a vacuum pump 23 through a conduit 24, a cooler 25 and a conduit 26. The permeated side of the gas-separating membrane is maintained under a reduced pressure, to accelerate the permeation of the permeated fraction containing the concentrated water vapor. The permeated fraction discharged from the permeated side through the conduit 24 is cooled and converted to a liquid by the cooler 25, and the resultant liquid containing the concentrated water is withdrawn to the outside of the apparatus through a trap 27.

The feed side of the gas-separating membrane is connected to a tank 28 for receiving a concentrated lower alcohol liquid 28a through a valve 29, a conduit 30 and a cooler 31.

The non-permeated fraction remaining in the feed side of the gas-separating membrane is delivered from the module 18 through the valve 29 and a conduit 30 and cooled and converted to a concentrated lower alcohol liquid 28a and received in the tank 28.

The concentrated lower alcohol liquid 28a is recovered to the outside of the apparatus through a pump 32 and a conduit 33. Preferably, at least a portion of the recovered concentrated lower alcohol liquid 28a is continuously or intermittently returned into the vapor treating vessel 1 through the pump 32 and a conduit 34 connected to the conduit 33, and is reused for vapor drying the article 6.

The concentrated lower alcohol liquid 28a received in the tank 28 has a high purity of the lower alcohol and is substantially free from water. Therefore, the recovered concentrated lower alcohol liquid can be used for various industrial purposes.

In the process of the present invention, the vapor treating step is carried out by using, as a vapor drying medium, at least one member selected from aliphatic lower alcohols having 2 to 4 carbon atoms, for example, ethyl alcohol, n-propyl alcohol, isopropyl alcohol, n-butyl alcohol and isobutyl alcohol. A most preferable lower alcohol for the process of the present invention is isopropyl alcohol.

The vapor treating step is also carried out by vaporizing the lower alcohol from the lower alcohol-based liquid in the tank space of the vapor treating vessel, and vapor treating the water-wetted article with the vapor of the lower alcohol at a temperature of 78° C. to 120° C. under the ambient atmospheric pressure.

In the vaporizing procedure, the mixed liquid of the lower alcohol with water is converted to the corresponding mixed vapor at a temperature of 78° C. to 200° C. under a pressure of 0 to 10 kg/cm$^2$ G.

In the gas-separating step, the gas-separating membrane preferably has a permeation rate of water vapor [PH$_2$O] of $\times$ 1.0 $\times$ 10$^{-4}$ Ncm$^3$/cm$^2$·sec·cmHg or more, more preferably 5 $\times$ 10$^{-4}$ to 20 $\times$ 10$^{-4}$ Ncm$^3$/cm$^2$·sec·cmHg at a temperature of 120° C.

Also, the gas-separating membrane preferably exhibits a ratio (PH$_2$O/P$_{ROH}$) of a permeation rate of water vapor (PH$_2$O) to a permeation rate of the lower alcohol vapor (P$_{ROH}$) of from 100 to 20,000, more preferably 500 to 8,000. Further, preferably the gas-separating membrane is usable at a high temperature in a wide range of from 50° C. to 200° C., more preferably from 80° C. to 160° C.

Furthermore, the gas-separating membrane preferably comprises a heat resistant polymer selected from the group consisting of, for example, aromatic polyimide resins, aromatic polyamide resins, and polysulfon resins. Preferably, the heat resistant gas-separating membrane is an asymmetric membrane having a dense layer, which is very thin, and a porous layer which serves as a support for the dense layer and has a relatively large thickness. More preferably, the gas-separating membrane usable for the present invention is an asymmetric gas-separating hollow fiber comprising an aromatic polyimide resin.

In the gas-separating step of the process of the present invention, the mixed vapor of the lower alcohol and water is fed to the feed side of the gas-separating membrane preferably at a temperature higher than the boiling temperatures of the lower alcohol and water.

The permeated side of the gas-separating membrane is preferably under a reduced pressure of 500 torr or less, more preferably 200 torr or less.

Where at least a portion of the recovered concentrated lower alcohol liquid is returned to the vapor treating vessel, the temperature of the concentrated lower alcohol liquid is preferably adjusted to a temperature of at least 10° C., more preferably at least 20° C., below the lowest of the boiling temperatures of the lower alcohol and water. When the lower alcohol is isopropyl alcohol, the condensed lower alcohol liquid is preferably returned at a temperature of 10° to 90° C., more preferably 30° to 80° C., to the vapor treating vessel.

The process and apparatus of the present invention is able to recover a lower alcohol having a high purity from a mixed liquid thereof with water, derived from a vapor drying process and apparatus in which a water-washed article, for example, a precision electronic component such as a printed circuit board, semiconductor wafer, electronic parts and liquid crystal base plates, and a lens, is dried by a vapor of the lower alcohol.

EXAMPLES

The present invention will be further explained by the following examples.

EXAMPLE 1

A vapor treating step was carried out in the vapor treating vessel 1 as indicated in FIG. 1, by vapor treating about 60,000 lenses having a diameter of 40 mm, produced from a glass and wetted by a large amount of water, by a vapor of isopropyl alcohol (IPA) at a temperature of 130° C. under the ambient atmospheric pressure. This treatment was continued for about one week, while replenishing the vapor treating vessel 1 with fresh isopropyl alcohol liquid from a tank 9. Referring to FIG. 1, the fresh isopropyl alcohol liquid at the location ① in the conduit 11 had the temperature, pressure, composition, and flow rate as shown in Table 1. Also, a plurality of lenses held by a holder are introduced into the vapor treating vessel as shown in an arrow in FIG. 1. The water on the lenses had, at the location ② in FIG. 1, the temperature, pressure, composition and flow rate as shown in Table 1.

The concentration of isopropyl alcohol in the isopropyl alcohol-based liquid 3 in the tank space 2 was maintained at a level of 95% by weight or more in average.

The resultant mixed liquid of isopropyl alcohol and water was collected by the collector 7, cooled by the cooler 16, and received by the tank 12.

The concentration of isopropyl alcohol in the mixed liquid 12a in the tank 12 was maintained at an average value of 85% by weight or more.

The mixed liquid was introduced from the tank 12 to the vaporizer 43, through the pump 46 and the conduit 47. The mixed liquid had, at the location ③ in the conduit 47, the temperature, pressure, composition and flow rate as shown in Table 1.

The mixed liquid was vaporized at a temperature of 100° C. under a pressure of 1.0 kg/cm²·G, and the resultant mixed vapor was overheated at a temperature of 120° C. under a pressure of 1.0 kg/cm²·G, and introduced into the gas-separating module 18 through the conduit 22.

The overheated mixed vapor had, at the location ④ in the conduit 22, the temperature, pressure, composition and flow rate as indicated in Table 1.

The gas-separating module 18 was provided with a number of gas-separating hollow fiber membranes available under the trademark of UBE Polyimide Membrane Type D, from UBE INDUSTRIES, LTD., and having a total surface area of 4.80 m². The membranes had a water vapor ($PH_2O$) permeation rate of $9 \times 10^{-4}$ Ncm²/cm²·sec·cmHg at a temperature of 120° C., and a ratio ($PH_2O/P_{IPA}$) of a water vapor permeation rate ($PH_2O$) to an isopropyl alcohol permeation rate ($P_{IPA}$) of 4,000.

In the gas-separating procedure, the permeated side of the gas-separating membrane was maintained under a reduced pressure of 60 torr.

The mixed vapor was separated into a permeated fraction and a non-permeated fraction.

The permeated fraction was discharged from the permeated side of the gas-separating membrane through the conduit 24, and liquefied by the cooler 25 at a temperature of 40° C. The permeated fraction had, at the location ⑤ in the conduit 24, the temperature, pressure, composition and flow rate as shown in Table 1.

Also, the non-permeated fraction was introduced from the feed side of the gas-separating membrane into the cooler 31 through the conduit 30, and liquefied by the cooler, and the resultant liquid was received by the tank 28.

The non-permeated fraction had, at the location ⑥ in the conduit 30, the temperature, pressure, composition and flow rate as indicated in Table 1.

The cooled liquid by the cooler 31 had, at the location ⑦ between the cooler 31 and the tank 28, the temperature, pressure, composition and flow rate as indicated in Table 1.

The recovered isopropyl alcohol liquid had a concentration of isopropyl alcohol of 99.5% by weight.

TABLE 1

| Item | | ① | ② | ③ | ④ | ⑤ | ⑥ | ⑦ |
|---|---|---|---|---|---|---|---|---|
| State | | Liquid | Liquid | Liquid | Vapor | Vapor | Vapor | Liquid |
| Temperature (°C.) | | 30 | 30 | 30 | 130 | 120 | 130 | 30 |
| Pressure (kg/cm² G) | | 0 | 0 | 1.5 | 1.5 | (60 torr) | 1.5 | 0 |
| Composition | Water | 0 | 100 | 15.0 | 15.0 | 93.6 | 0.5 | 0.5 |
| (% by wt) | IPA | 100.0 | 0 | 85.0 | 85.0 | 6.4 | 99.5 | 99.5 |
| Flow rate | Water | 0.0 | 0.38 | 0.45 | 0.45 | 0.44 | 0.01 | 0.01 |
| (kg/hr) | IPA | 0.50 | 0 | 2.55 | 2.55 | 0.03 | 2.52 | 2.52 |
| | Total | 2.62 | 0.38 | 3.00 | 3.00 | 0.47 | 2.53 | 2.53 |

EXAMPLE 2

The same procedures as in Example 1 were carried out, with the following exceptions.

1. The lenses were replaced by semiconductor wafers covered by a large amount of water and having a size of 147 mm, which were supplied at a supply rate of 300 pieces/hr to the vapor treating vessel.

2. The recovered isopropyl alcohol 28a in the tank 28 was returned into the tank space 2 of the vapor treating vessel 1 through a conduit 34, to reduce the replenishing amount of isopropyl alcohol liquid 8 fed from the tank 9 into the tank space 2.

3. The total surface area of the gas-separating membranes was 2.79 m².

4. The average concentration of isopropyl alcohol in the isopropyl alcohol based liquid 3 in the tank space 2 of the vapor treating vessel 1 was maintained at a level of 97% by weight or more.

5. The average concentration of the mixed liquid received in the tank 12 was maintained at a level of 90% by weight or more.

The liquids or vapors at the locations ① to ⑦ had the temperatures, pressures, compositions and flow rates as shown in Table 2.

TABLE 2

| Item | | ① | ② | ③ | ④ | ⑤ | ⑥ | ⑦ |
|---|---|---|---|---|---|---|---|---|
| State | | Liquid | Liquid | Liquid | Vapor | Vapor | Vapor | Liquid |
| Temperature (°C.) | | 30 | 30 | 30 | 130 | 130 | 130 | 30 |
| Pressure (kg/cm² G) | | 1.0 | 0 | 1.0 | 1.0 | (60 torr) | 1.0 | 0 |
| Composition | Water | 0.01 | 100 | 3.0 | 3.0 | 90.2 | 1.0 | 1.0 |
| (% by wt) | IPA | 99.9 | 0 | 97.0 | 97.0 | 9.8 | 99.0 | 99.0 |
| Flow rate | Water | 0.0 | 0.12 | 0.18 | 0.18 | 0.12 | 0.06 | 0.06 |
| (kg/hr) | IPA | 0.013 | 0 | 5.82 | 2.82 | 0.013 | 5.81 | 5.81 |
| | Total | 0.013 | 0.12 | 6.00 | 6.00 | 0.133 | 5.87 | 5.87 |

Tables 1 and 2 clearly show that the recovered isopropyl alcohol liquid 28a at the location ⑦ had a very high purity and was substantially free from water, and therefore, the recovered isopropyl alcohol liquid was able to be returned to, and re-used for, the vapor treating step. Also, an undesirable increase in the concentration of water in the vapor treating vessel was substantially completely prevented throughout the vapor treating procedure for one week. Further, the concentration of isopropyl alcohol in the isopropyl alcohol-based liquid 3 in the tank space 2 was maintained at a high level of 95% by weight or more.

In Examples 1 and 2, it was confirmed that the lenses and semiconductor wafers were completely dried, and thus were absolutely free from water.

Also, it was confirmed that the gas-separating membrane in the module was highly effective for selectively removing water from a mixed vapor of a lower alcohol and water, and for recovering the lower alcohol with a high purity, at a low energy consumption, a low cost, and a high stability over a long term.

We claim:

1. A process for recovering a lower alcohol from a mixture thereof with water, comprising the steps of:
   (A) vapor-treating at least one article wetted at the surface thereof with water, and placed in a vapor treating vessel with a vapor of a lower alcohol generated from a corresponding lower alcohol-based liquid to vapor dry the article, while allowing the vapor of the lower alcohol to be condensed on the surface of the article;
   (B) feeding a mixed liquid of the lower alcohol with water comprising the condensed liquid, into a vaporizer to provide a mixed vapor of the lower alcohol with water;
   (C) feeding the mixed vapor of the lower alcohol with water into a gas-separating module comprising therein at least one gas-separating membrane which allows a selective permeation of water vapor therethrough from a feed side to a permeated side thereof, to separate the mixed vapor into a non-permeated vapor fraction comprising the lower alcohol in an increased concentration and water in a decreased concentration and a permeated vapor fraction containing water in an increased concentration;
   (D) recovering the non-permeated vapor fraction from the feed side of the gas-separating membrane, while discharging the permeated vapor fraction from the permeated side of the gas-separating membrane; and
   (E) cooling the recovered non-permeated vapor fraction to convert it to a liquid containing the lower alcohol in an increased concentration.

2. The process as claimed in claim 1, wherein the lower alcohol is selected from aliphatic lower alcohols having 2 to 4 carbon atoms.

3. The process as claimed in claim 1, wherein the lower alcohol-based liquid in the vapor treating vessel contains the lower alcohol in a concentration of 90% by weight or more.

4. The process as claimed in claim 1, wherein the mixed liquid of the lower alcohol and water, to be fed into the vaporizer contains the lower alcohol in a concentration of 75% by weight or more.

5. The process as claimed in claim 1, wherein the mixed liquid to be fed to the vaporizer is a mixture of the condensed liquid with a portion of the lower alcohol-based liquid withdrawn from the vapor treating vessel.

6. The process as claimed in claim 1, wherein the gas-separating membrane has a permeation rate of water vapor [PH$_2$O] of $1.0 \times 10^{-4}$ Ncm$^3$/cm$^2$·sec·cmHg or more, at a temperature of 120° C.

7. The process as claimed in claim 1, wherein the gas-separating membrane exhibits a ratio (PH$_2$O/P$_{ROH}$) of a permeation rate of water vapor (PH$_2$O) to a permeation rate of the lower alcohol vapor (P$_{ROH}$) of from 100 to 20,000.

8. The process as claimed in claim 1, wherein the gas-separating membrane is usable at a temperature of from 50° C. to 200° C.

9. The process as claimed in claim 1, wherein the gas-separating membrane comprises a heat resistant synthetic resin selected from the group consisting of aromatic polyimide resins, aromatic polyamide resins and polysulfon resins.

10. The process as claimed in claim 1, wherein the gas-separating membrane is an asymmetric membrane having a dense layer and a porous layer.

11. The process as claimed in claim 1, wherein the gas-separating membrane is an asymmetric gas-separating hollow fiber comprising an aromatic polyimide, resin.

12. The process as claimed in claim 1, wherein the mixed vapor of the lower alcohol and water is fed into the gas-separating module at a temperature higher than the boiling temperatures of the lower alcohol and water.

13. The process as claimed in claim 1, wherein the mixed vapor of the lower alcohol and water is fed into the gas-separating module under a pressure of from 1 to 10 kg/cm$^2$.

14. The process as claimed in claim 1, wherein the permeated side of the gas-separating membrane is under a reduced pressure of 500 torr or less.

15. The process as claimed in claim 1, wherein at least a portion of the recovered liquid containing the concentrated lower alcohol liquid is returned into the vapor treating vessel.

* * * * *